United States Patent
Cronin et al.

(10) Patent No.: US 8,608,751 B2
(45) Date of Patent: Dec. 17, 2013

(54) ASSEMBLY SYSTEM FOR ORTHOPEDIC COMPONENTS

(75) Inventors: Shaun R. Cronin, Fort Wayne, IN (US); Scott E. Dykema, Warsaw, IN (US); Jeff Blaylock, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 811 days.

(21) Appl. No.: 11/611,197

(22) Filed: Dec. 15, 2006

(65) Prior Publication Data

US 2008/0147196 A1 Jun. 19, 2008

(51) Int. Cl.
*A61B 17/88* (2006.01)
*A61B 17/84* (2006.01)
*A61B 17/56* (2006.01)
*A61F 2/38* (2006.01)
*A61F 2/46* (2006.01)

(52) U.S. Cl.
USPC .......... 606/99; 606/86 R; 606/300; 623/20.14

(58) Field of Classification Search
USPC .................. 606/57, 99, 86 R–88, 100, 290, 606/300–303, 305–308, 320, 322, 328; 623/20.14, 20.15, 20.21, 20.32, 20.34, 623/22.12; 411/400, 408–410, 485, 546; 16/2.1, 2.3, 2.4
See application file for complete search history.

(56) References Cited

U.S. PATENT DOCUMENTS

| | | | | |
|---|---|---|---|---|
| 419,642 A | * | 1/1890 | Cornog .................... | 174/155 |
| 3,212,387 A | * | 10/1965 | Madansky ................ | 411/371.2 |
| 3,861,731 A | * | 1/1975 | Young ..................... | 114/221 R |
| 4,936,172 A | * | 6/1990 | Jackson ................... | 81/451 |
| 6,238,435 B1 | * | 5/2001 | Meulink et al. .......... | 623/22.12 |
| 6,248,108 B1 | * | 6/2001 | Tormala et al. .......... | 606/318 |
| 2004/0073315 A1 | * | 4/2004 | Justin et al. ............. | 623/20.15 |

* cited by examiner

*Primary Examiner* — Michael T Schaper
(74) *Attorney, Agent, or Firm* — Schwegman, Lundberg & Woessner P.A.

(57) ABSTRACT

An assembly system configured to seat a first orthopedic component having either a male taper or a female taper with a second orthopedic component having the other of a male taper or a female taper. In one embodiment, the assembly system includes a taper seating connector having a fastener and a bushing moveable retained on the fastener. The fastener may be connected to the first orthopedic component and the bushing may be positioned adjacent the second orthopedic component. The corresponding tapers on the first and second orthopedic components may be configured to secure the first and second orthopedic components together. Thus, by exerting a sufficient force on the bushing, the bushing will move along the fastener, transferring the force to the second orthopedic component. In this manner, the corresponding tapers of the first and second orthopedic components may be seated.

13 Claims, 6 Drawing Sheets

FIG_5

FIG_6

FIG_7

ASSEMBLY SYSTEM FOR ORTHOPEDIC COMPONENTS

BACKGROUND OF THE INVENTION

1. Field of the Invention

The present invention relates to an assembly system, and, more particularly, to an assembly system for assembling orthopedic components.

2. Description of the Related Art

Orthopedic components, such as prostheses, are commonly utilized to repair and/or replace damaged bone and tissue in the human body. For example, hip prostheses may be implanted to replace damaged or destroyed bone in the femur and/or acetabulum and to recreate the natural, anatomical articulation of the hip joint. Additionally, prostheses may be formed as modular prostheses. Modular prostheses have several individual, distinct components which are connected together to form a final, implanted prosthesis.

To connect the individual modular components together to form the final, implanted prosthesis, specialized tools are often needed. Depending on the design and connecting mechanism utilized in a specific modular prosthesis system, the specialized tools needed to connect the individual modular components may only function with a single modular prosthesis system. Therefore, a different set of tools are needed for each modular prosthesis system.

SUMMARY OF THE INVENTION

The present invention relates to an assembly system, and, more particularly, to an assembly system configured for assembling orthopedic components. The assembly system is configured to seat a first orthopedic component having either a male taper or a female taper with a second orthopedic component having the other of a male taper or a female taper. In one embodiment, the assembly system includes a taper seating connector having a fastener and a bushing moveable retained on the fastener. The fastener may be connected to the first orthopedic component and the bushing may be positioned adjacent the second orthopedic component. By exerting a sufficient force on the bushing, the bushing will move along the fastener, transferring the force to the second orthopedic component. This may cause the second orthopedic component to move toward the first orthopedic component. In this manner, the corresponding tapers of the first and second orthopedic components may be seated.

In another embodiment, the assembly system includes a taper seating tool. The taper seating tool may have a rod and a sleeve. The rod may be configured to attach to one of the fastener and the bushing of the taper seating connector. Similarly, the sleeve may be configured to abut the other of the fastener and the bushing. By moving the rod and/or the sleeve of the taper seating tool relative to one another, a force is exerted on at least one of the fastener and the bushing of the taper seating connector. When the taper seating connector is positioned as described above with respect to the first and second orthopedic components, the force exerted by the taper seating tool on the taper seating connector will cause movement of the fastener and/or bushing of the taper seating connector. This movement will result in corresponding movement of the first and/or second orthopedic components and the seating of the tapers of the first and second orthopedic components.

In one form thereof, the present invention provides a taper seating connector, including a fastener having a shaft and a hooked head, the shaft connectable to a first orthopedic component having one of a male tapered surface and a female tapered surface; a bushing retained on and moveable along the shaft of the fastener, the bushing positioned adjacent a second orthopedic component when the fastener is connected to the first orthopedic component, wherein the second orthopedic component has the other of the one of a male tapered surface and a female tapered surface, whereby movement of one of the fastener and the bushing results in corresponding movement of one of the first and second orthopedic components.

In another form thereof, the present invention provides in combination a taper seating connector including a fastener and a bushing, the fastener connectable to a first orthopedic component having one of a male tapered surface and a female tapered surface, the bushing positioned adjacent a second orthopedic component when the fastener is connected to the first orthopedic component, the second orthopedic component having the other of the one of a male tapered surface and a female tapered surface; and a taper seating tool having a rod and a sleeve, wherein at least one of the rod and the sleeve are moveable relative to the other of the rod and the sleeve, the rod configured for attachment to the fastener of the taper seating connector, the sleeve configured to abut the bushing of the taper seating connector when the rod is attached to the fastener, whereby movement of at least one of the rod and the sleeve relative to the other of the rod and the sleeve seats the male tapered surface and the female tapered surface.

In yet another form thereof, the present invention provides a method of seating orthopedic components including the steps of securing a taper seating connector having a fastener and a bushing to a first orthopedic component; positioning the taper seating connector adjacent a second orthopedic component; attaching a taper seating tool to the seating connector; actuating the taper seating tool to force at least one of the first orthopedic component and the second orthopedic component toward the other one of the first orthopedic component and the second orthopedic component to seat the first and second orthopedic components.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention any manner.

DETAILED DESCRIPTION OF THE INVENTION

Figures 1, 2, 3:
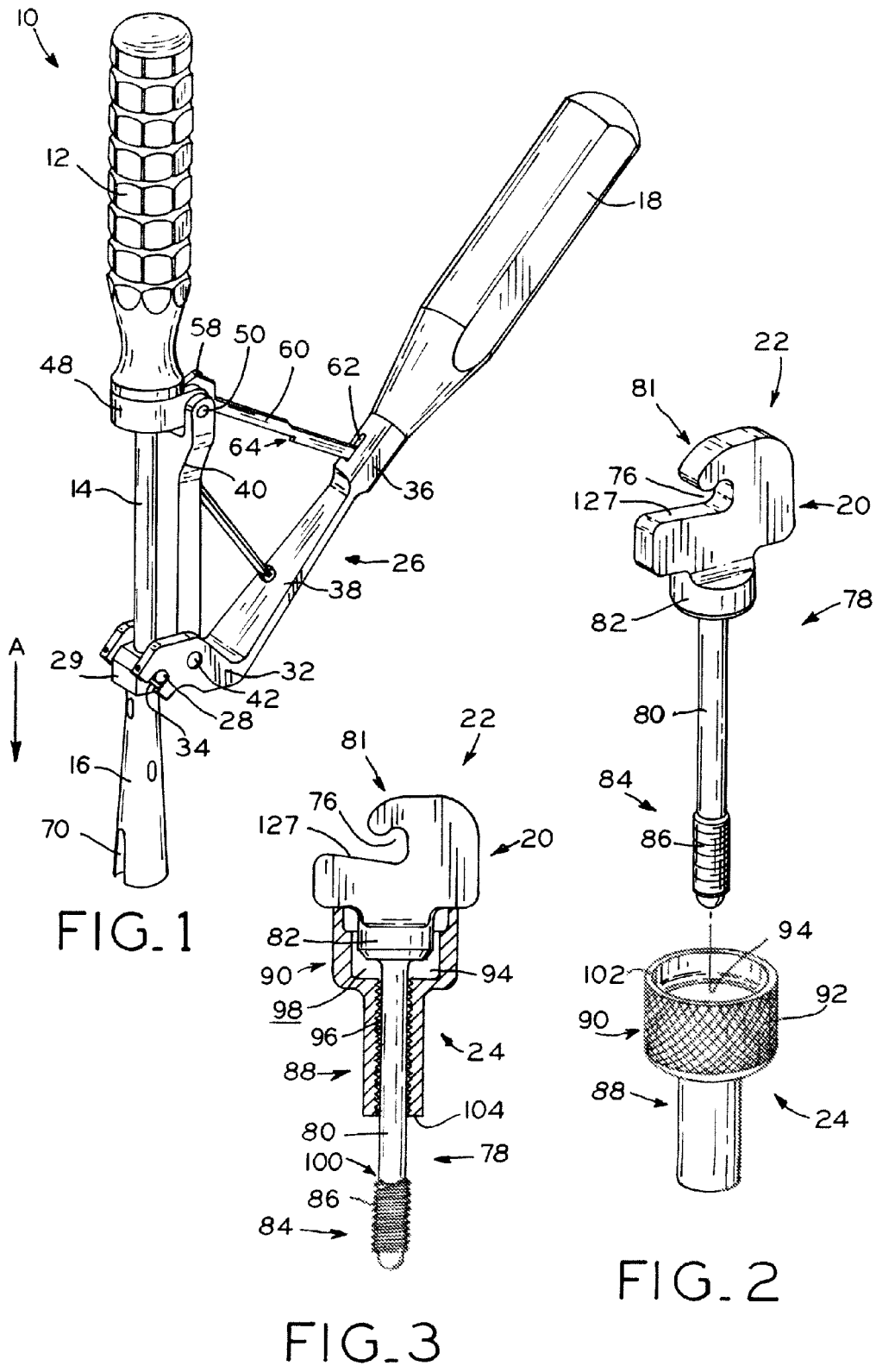
FIG. 1 is a perspective view of a taper seating tool according to one embodiment of the present assembly system.
FIG. 2 is an exploded perspective view of a taper seating connector of the present assembly system.
FIG. 3 is a cross-sectional view of the taper seating connector of FIG. 2.
Figure 4:
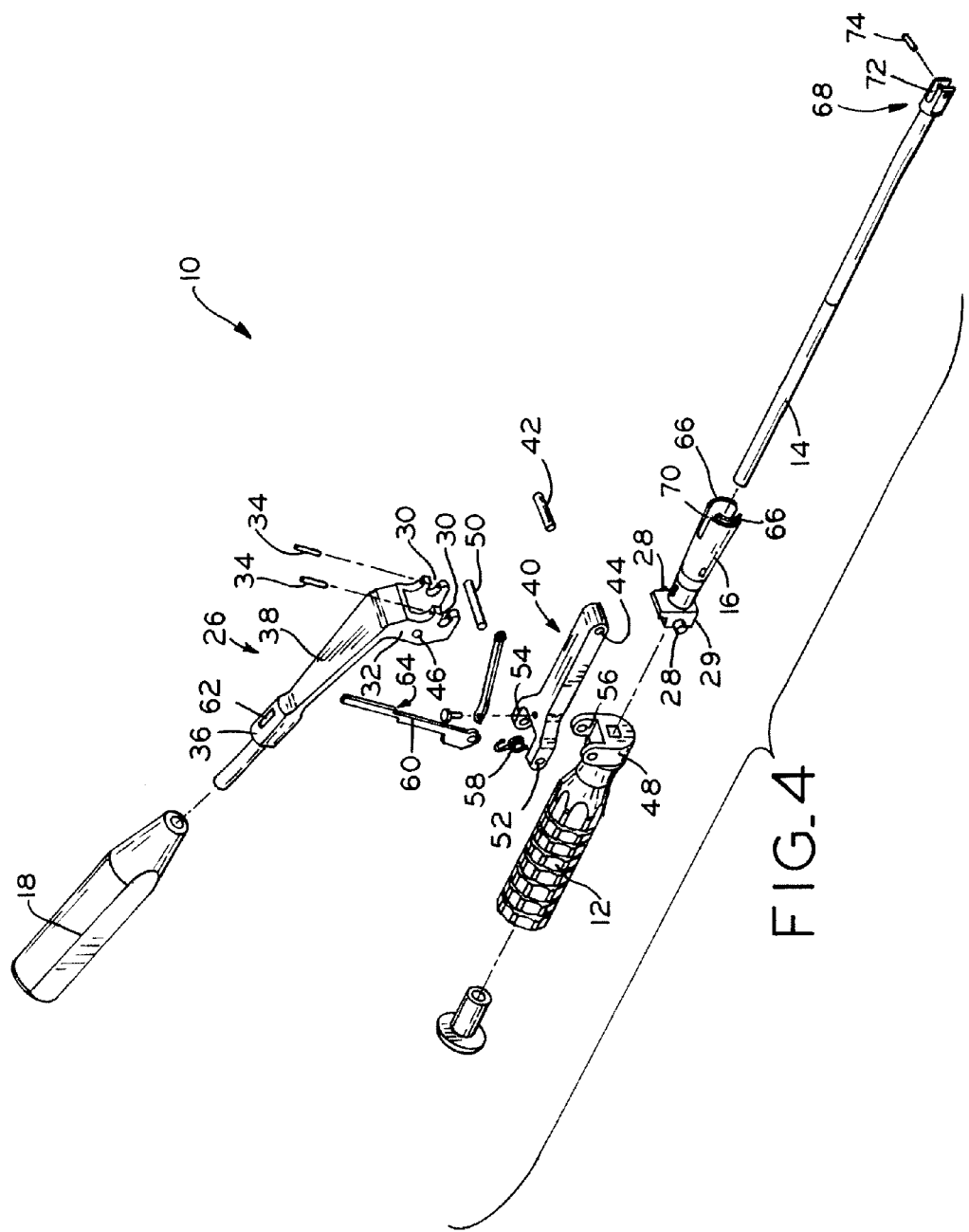
FIG. 4 is an exploded perspective view of the taper seating tool of FIG. 1.

FIGS. 1 and 4 depict taper seating tool 10 of the present assembly system. Taper seating tool 10 includes fixed handle 12 rigidly secured to fixed rod 14. Sleeve 16 surrounds at least a portion of fixed rod 14 and is moveable along the longitudinal axis thereof. As described in detail below, when moveable handle 18 is rotated toward fixed handle 12, sleeve 16 moves downward along fixed rod 14 in the direction of arrow A. Thus, when fixed rod 14 is secured to head 20 of taper seating connector 22 (FIGS. 2, 3, and 5-8) movement of sleeve 16 exerts a downward force on bushing 24 of taper seating connector 22 to seat the corresponding tapers of orthopedic components, as described in detail below.

Referring to FIGS. 1 and 4, sleeve 16 of taper seating tool 10 is connected to moveable handle 18 via work arm 26. Specifically, projections 28, extending from opposing sides of head 29 of sleeve 16, are received within grooves 30 (FIG. 4) formed in pivot portion 32 of work arm 26. Work arm 26 is retained on projections 28 by retention pins 34. Additionally, moveable handle 18 is secured to work arm 26 at end 36. Extending between pivot portion 32 and end 36 of work arm 26 is connecting portion 38. Connecting portion 38 tapers along its length, so that the width of connecting portion 38 decreases as connecting portion 38 approaches end 36 of work arm 26. The taper of connecting portion 38 allows for connecting portion 38 to bend when a sufficient force is exerted on moveable handle 18. This bending causes a substantially even distribution of the stress, caused by the force exerted on moveable handle 18, along the length of connecting portion 38 which provides a tactile feedback to the surgeon as discussed in detail below. Advantageously, the substantially even distribution of stress along the entire length of connecting portion 38 may increase the useful life of taper seating tool 10.

As shown in FIGS. 1 and 2, work arm 26 is further connected to fixed handle 12 via link 40. Link 40 is connected to pivot portion 32 of work arm 26 via link pin 42, which extends through aperture 44 (FIG. 4) of link 40 and apertures 46 of pivot portion 32 (FIG. 4). The opposing end of link 40 is connected to collar 48. Collar 48 substantially surrounds fixed rod 14 and is positioned adjacent to fixed handle 12. In one exemplary embodiment, collar 48 and handle 14 are formed as an integral, monolithic component. Link 40 is attached to collar 48 by link pin 50 extending through apertures in Y-arms 52, 54 (FIG. 2) and corresponding apertures in projections 56 of collar 48. Thus, when moveable handle 18 is rotated toward fixed handle 12, work arm 26 is rotated about link pin 42. Rotation of work arm 26 about link pin 42 causes pivot portion 32 to correspondingly rotate and exert a force on projections 28 of sleeve 16. This force results in movement of sleeve 16 in the direction of arrow A (FIG. 1).

As shown in FIG. 4, spring 58 and lock arm 60 are retained on link pin 50 and secured between Y-arms 52, 54 of link 40. Spring 58 is connected to and exerts a downward biasing force on lock arm 60, which is configured to pivot about link pin 50. As shown in FIG. 1, lock arm 60 extends through slot 62 in end 36 of work arm 26. Lock arm 60 further includes projection 64, which forms a detent with slot 62. Specifically, when moveable handle 18 is rotated about link pin 42 and advanced toward fix handle 14, lock arm 60 will be correspondingly advanced through slot 62. As handle 38 continues toward handle 14, projection 64 will pass through slot 62 and will move downward due to the biasing force of spring 58. Thus, when movement of movable handle 38 ceases, the biasing force of spring arm 61 will rotate work arm 26 and moveable handle 18 away from handle 14. When end 36 of work arm 26 contacts projection 64 of lock arm 60, further movement of moveable handle 18 away from fixed handle 12 will be prevented.

Advantageously, the use of lock arm 60 causes a change in the center of gravity of taper seating tool 10 and allows taper seating tool 10 to stand in an upright position on compression surface 66 (FIG. 4). Thus, a surgeon does not need to constantly hold taper seating tool 10 upright when it is in the "locked" position. To unlock lock arm 60, the surgeon simply lifts up on lock arm 60 with sufficient force to overcome the biasing force of spring 58. Once projection 60 of lock arm 60 is positioned within slot 62, moveable handle 18 may be rotated away form fixed handle 12 without encountering a further impediment.

To facilitate the attachment of taper seating tool 10 to taper seating connector 22 (FIGS. 2, 3, and 6-8), fixed rod 14 and sleeve 16 include catch end 68 and passage 70, respectively. While depicted and described herein as being configured for attachment to taper seating connector 22, shown in FIGS. 2 and 3, tapered seating tool 10 may also be configured for attachment directly to an orthopedic component or to a seating connector having a different configuration. Slot 72, extending partially through catch end 68, is aligned with passage 70 to accommodate head 20 of taper seating connector 22. Extending across slot 72 of catch end 68 is bar 74. Bar 74 is configured for receipt within catch 76 of head 20, as described in detail below. Advantageously, by utilized catch end 68 of fixed rod 14, taper seating tool 10 may be connected to any taper seating connectors having catch 76 or a similar attachment mechanism. Thus, taper seating tool 10 may be connected to taper seating connectors 12 which are configured for different modular prosthesis systems. This allows for a single taper seating tool 10 to be interchangeably used with numerous prosthesis systems, lessening both the cost of manufacturing taper seating tool 10 and the cost of inventorying the same.

Referring to FIGS. 2 and 3 and as discussed briefly above, taper seating connector 22 of the present assembly system includes fastener 78 and bushing 24. Fastener 78 includes shaft 80 and head 20 connected via neck 82. Hook 81 of head 20 forms catch 76 therein. Additionally, threaded portion 84, having threads 86 thereon, is formed on shaft 80 of fastener 78. Bushing 24 of taper seating connector 22 includes body 88 and barrel 90. Knurled surface 92 of barrel 90 facilitates the grasping and positioning of taper seating connector 22. Extending through bushing 24 is aperture 94. As shown in FIG. 3, body 88 defines a portion of aperture 94 having threads 96 formed therealong. Additionally, barrel 90 of bushing 24 includes counterbore 98 which also forms a portion of aperture 94.

Referring to FIG. 3, taper seating connector 22 is assembled by capturing bushing 24 on fastener 78. Specifically, threads 86 of fastener 78 are threaded along corresponding threads 96 through aperture 94 of bushing 24. In one exemplary embodiment, once threads 86 have passed along the entirety of threads 96, uppermost thread 86 is crimped, as shown at 100, to prevent the separation of fastener 78 and bushing 24. With taper seating connector 22 configured as shown in FIG. 3, bushing 24 may move axially along shaft 80. Specifically, bushing 24 may move from a position in which head 20 of fastener 78 contacts upper surface 102 (FIG. 2) of bushing 24 to a position in which end surface 104 contacts the uppermost portion of threads 86.

Advantageously, by altering the design of threaded portion 86 of fastener 78 and bushing 24, taper seating connector 22 may be used with various modular prosthesis systems. Thus, by selecting the appropriate taper seating connector 22 for a particular modular prosthesis system, taper seating tool 10 may be used in conjunction with the appropriate taper seating connector 22 to seat the corresponding tapers of different components in the modular prosthesis system. This allows the seating of a plurality of different taper designs with a single taper seating tool 10.

Figure 5:
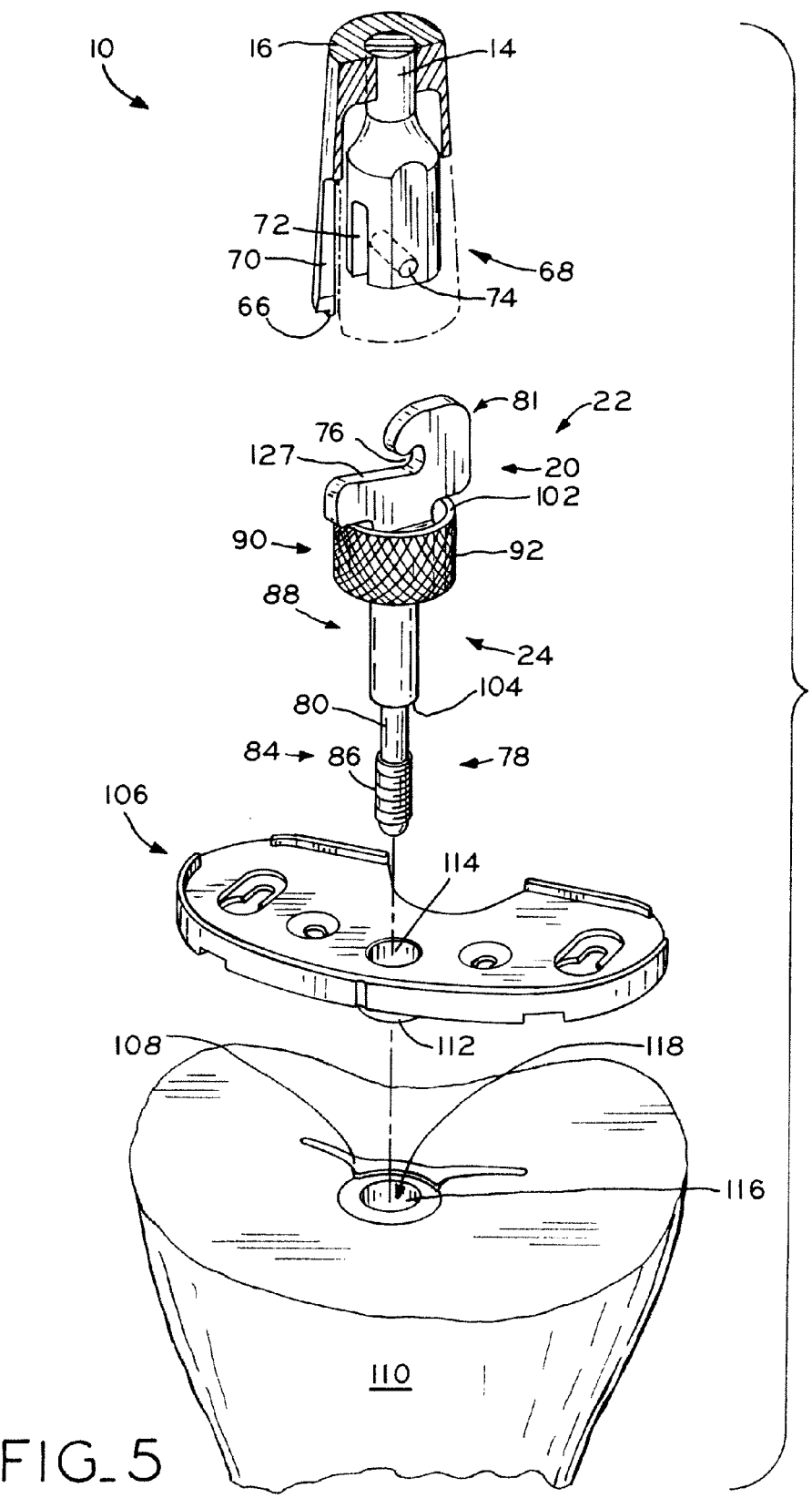
FIG. 5 is a fragmentary exploded perspective view depicting the taper seating tool of FIG. 1, the taper seating connector of FIG. 3, a tibial plate, a tibial keel, and a tibia.

By utilizing taper seating connector 22 in conjunction with tapered seating tool 10, orthopedic components having mating male and female tapers may be assembled by seating the mating tapers as described in detail below. Referring to FIG. 5, a portion of tapered seating tool 10 is shown positioned above taper seating connector 22. Additionally, tibial plate 106 and tibial keel 108, which is positioned within tibia 110, are also shown. While described and depicted herein with specific reference to tibial plate 106 and tibial keel 108, taper seat tool 10 and taper seat connector 12 may be utilized in conjunction with any orthopedic components having mating male and female tapers. As shown in FIG. 5, tibial plate 106 includes male tapered portion 112 having aperture 114 extending therethrough. Additionally, keel 108 includes female tapered surface 116 defining aperture 118 formed therein.

Figure 6:
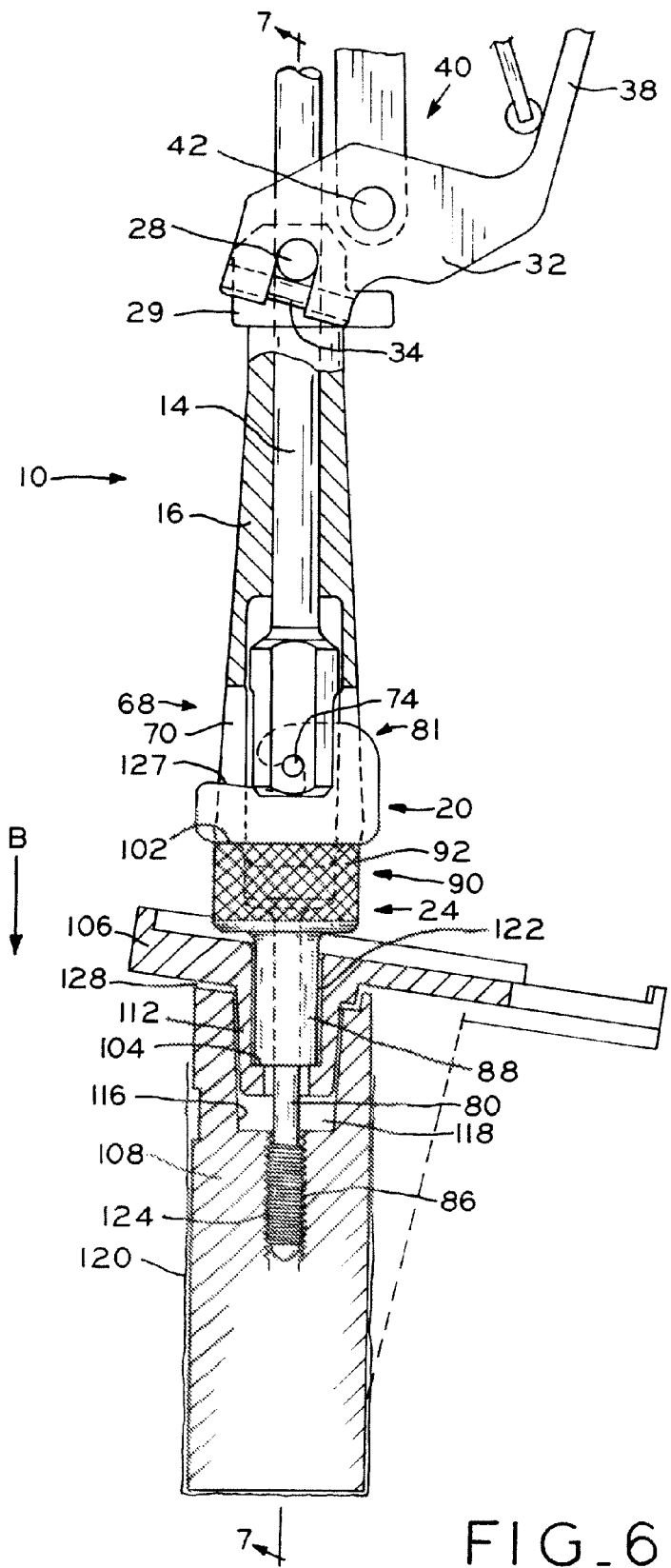
FIG. 6 is a fragmentary, partial cross-sectional view of the components of FIG. 5 depicting the corresponding tapers in an unseated position.
Figure 7:
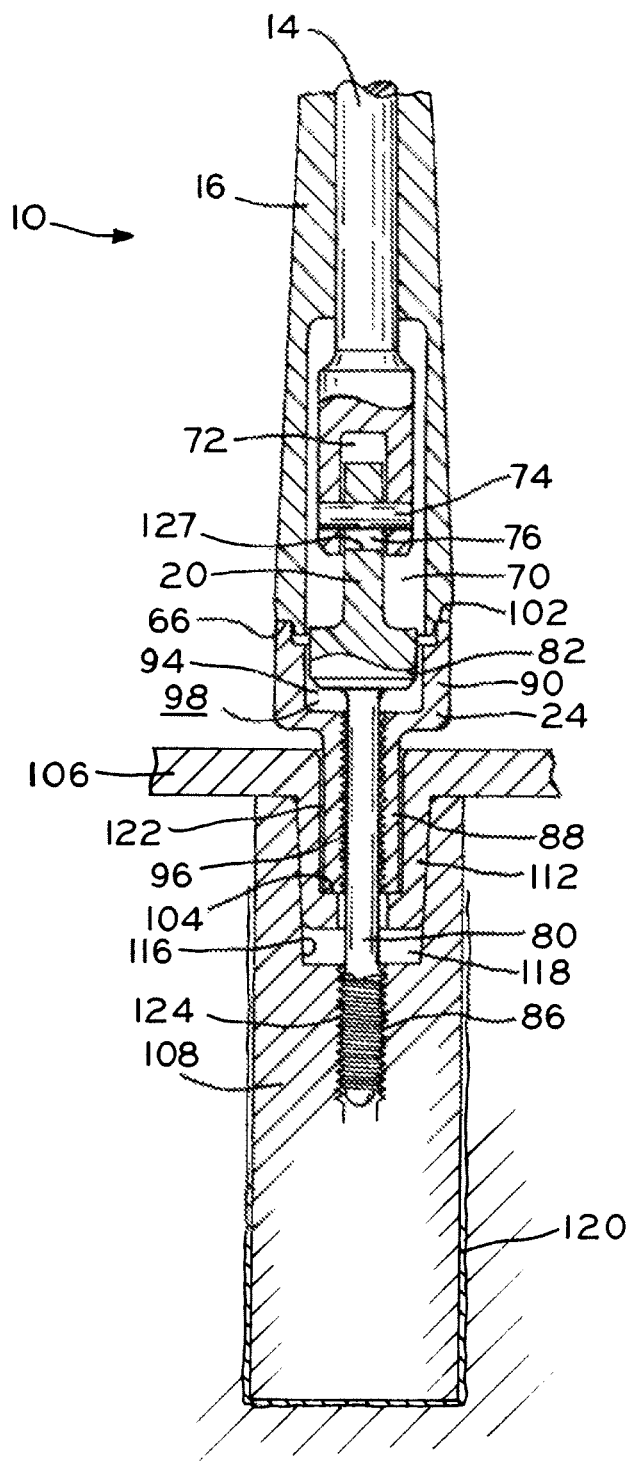
FIG. 7 is a fragmentary cross-sectional view of the components of FIG. 6 taken along line 7 of FIG. 6.
Figure 8:
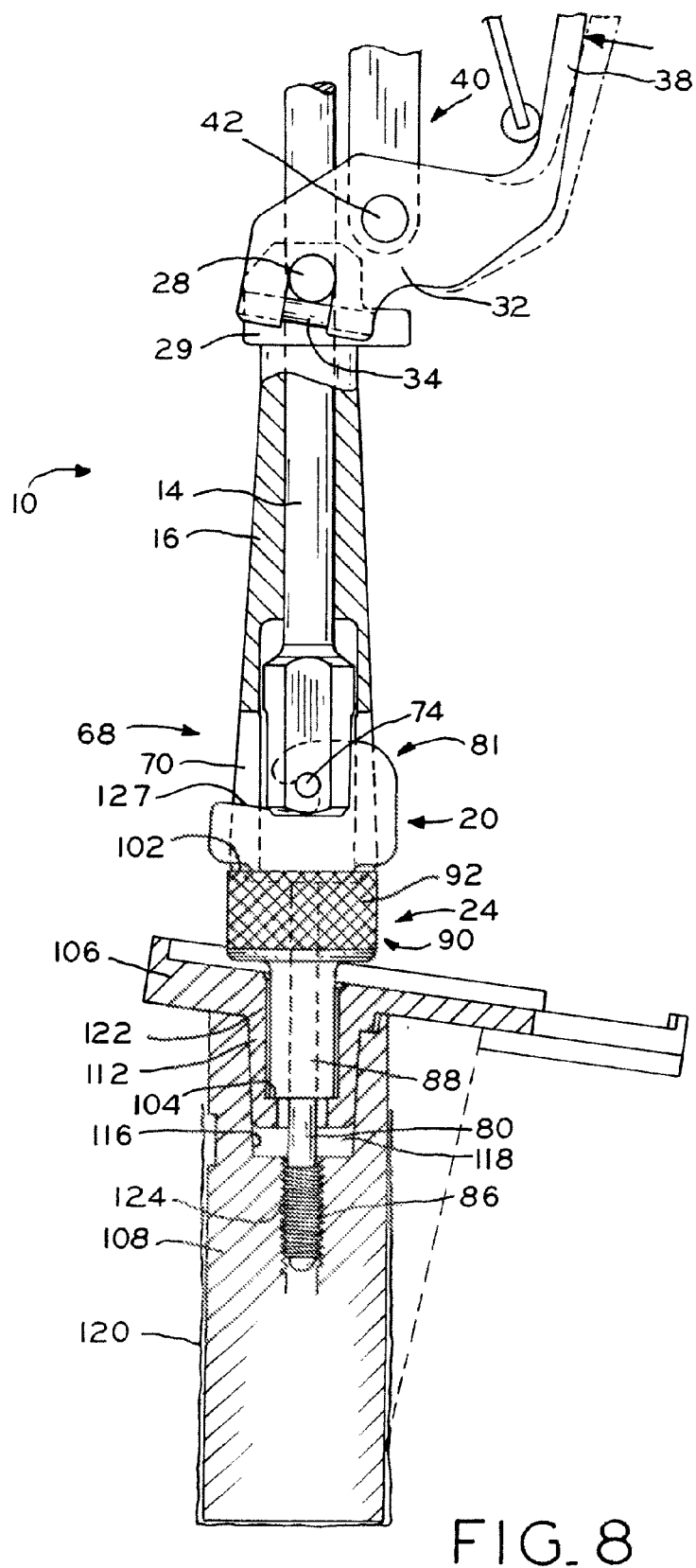
FIG. 8 is a fragmentary cross-sectional view of the apparatus of FIG. 7 depicting the corresponding tapers in a seated position.

To prepare the various components for attachment, as shown in FIGS. 6-8, keel 108 is first positioned within tibia 110 using any known surgical technique, which may include broaching, reaming, or otherwise preparing an aperture within tibia 110 which is configured to receive keel 108. Once the surgeon is satisfied with the ultimate positioning of keel 108 within tibia 110, bone cement 120 may be inserted between tibia 110 and keel 108. The male tapered portion 112 of the desired tibial plate 106 is then positioned within aperture 118 of keel 108. As shown in FIG. 5, taper seating connector 22 may then be inserted through aperture 114 of the tibial plate 106 with a portion of shaft 80, including threaded portion 84, extending through aperture 114. With taper seating connector 112 positioned within aperture 114 of tibial plate 106, end surface 104 (FIG. 3) of bushing 24 will rest against the bottom of counterbore 122 of aperture 114.

Once in this positioned, the surgeon may grasp head 20 of fastener 78 of taper seating connector 22 and rotate the same to cause mating engagement of threads 86 of thread portion 84 with threads 124 formed within aperture 118 of keel 108. As head 20 is rotated, fastener 78 will move further along threads 124 and will eventually contact upper surface 102 of bushing 24. Further rotation of head 20 will then begin seating male taper 112 with female tapered surface 116, as bushing 24 will begin to move downward, in the direction of arrow B (FIG. 6), with fastener 78. Once taper seating connector 22 is sufficiently tightened relative to keel 108 and plate 104, tapered seating tool 10 may be connected to taper seating connector 22. Specifically, head 20 of taper seating connector 22 is positioned within passage 70 of sleeve 16. In this configuration, head 20 is further received by fixed rod 14 via slot 72 of catch end 68. As catch end 68 is moved along surface 127 of head 20, bar 74 of catch end 68 is received and retained within catch 76 formed by hook 81 of taper seating connector 22. Advantageously, this design allows taper seating tool 10 to be secured to taper seating connector 22 in the position shown in FIGS. 6-8 and, alternatively, in a position which is rotated 180 degrees from the position depicted in FIGS. 6-8.

Once attached as shown in FIGS. 6-8, compression surface 66 of tapered seating tool 10 is in mating engagement with upper surface 102, shown in FIGS. 2 and 7, of bushing 24. Advantageously, once connected to taper seating connector 22, moveable handle 18 of taper seating tool 10 may be moved to the "locked" position described above. In this position, the stability of taper seating tool 10 along compression surface 66 significantly reduces the likelihood of the surgeon moving taper seating tool 10 and disturbing cement 120. Now, male taper 112 of tibial plate 106 and female tapered surface 116 are ready to be fully seated. Referring to FIG. 6, movable handle 38 of taper seating tool 10, shown in FIG. 1, is advanced toward fixed handle 12. As described above, movement of movable handle 38 toward fixed handle 12 results in work arm 26 pivoting about link pin 42 and causing rotation of grooves 30 about projections 28 of head 29 of sleeve 16. Rotation of grooves 30 about projections 28 results in a force being exerted on projections 28 of sleeve 16, causing downward movement of sleeve 16. This force is transferred to upper surface 102 of bushing 24 via compression surface 66.

Additionally, as discussed above, exerting a seating force on movable handle 38 causes work arm 26 to bend along connecting portion 38. This bending advantageously transfers the force along the entire length of connecting portion 38. Moreover, the bending of connecting portion 38 provides a visual indication to a surgeon that a seating force is being applied. In one exemplary embodiment, the bending of connecting portion 38 of work arm 26 allows moveable handle 18 to physically contact fixed handle 12 when the proper seating force, e.g., 1000 pounds, has been applied to taper seating connector 22. This provides both a visual and a tactile indication to a surgeon that a sufficient seating force has been applied. Due to the attachment of fixed rod 14 to keel 108, and the ability of bushing 24 to move along shaft 80, end surface 104 of bushing 24 presses against the bottom of counterbore 122 to force male taper 112 into seating engagement with female tapered surface 116 of keel 108. Referring to FIG. 8, male taper 112 of tibial plate 106 is shown seated with female tapered surface 116 of keel 108. Thus, tibial plate 106 is in direct contact with keel 108 and space 128 (FIG. 6) is absent.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. In combination, an assembly system comprising:
   a taper seating connector, including:
      a fastener having a shaft and a hooked head, said shaft having a threaded portion and a non-threaded portion, said threaded portion of said shaft adapted for threaded connection to a first orthopedic component having one of a male tapered surface and a female tapered surface; and
      a bushing having an external uppermost surface, an opposing end surface, and an aperture extending therethrough including a counterbore disposed between said external uppermost surface and an internal uppermost surface, said non-threaded portion of said shaft of said fastener configured to be positioned at least partially within said aperture of said bushing, said threaded portion of said shaft configured to be positioned entirely outside of said aperture adjacent to said end surface of said bushing, said hooked head of said fastener configured to be positioned outside of said aperture adjacent to said external uppermost surface of said bushing and extending beyond a periphery of said bushing, whereby said hooked head is configured to be available for securement, wherein said bushing is configured to be retained on and axially moveable along said non-threaded portion of said shaft of said fastener, said bushing is configured to be moveable along said non-threaded portion of said shaft between a first position in which said hooked head of said fastener contacts said external uppermost surface of said bushing and a second position in which a thread of said threaded portion of said shaft contacts said end surface of said bushing, said bushing configured to be positioned adjacent a second orthopedic component when said fastener is threadingly connected to the first orthopedic component, wherein the second orthopedic component has the other of said one of a male tapered surface and a female tapered surface, whereby movement of one of said fastener and said bushing results in corresponding movement of one of the first and second orthopedic components; and a taper seating tool having a rod and a sleeve, said rod configured for selective attachment to said fastener of said taper seating connector, said sleeve configured to selectively abut said bushing of said taper seating connector when said rod is attached to said fastener, whereby movement of at least one of said rod and said sleeve relative to the other of said rod and said sleeve seats said male tapered surface and said female tapered surface.

2. The assembly system of claim 1, wherein said hooked head comprises a catch configured for attachment to the taper seating tool.

3. The assembly system of claim 1, wherein movement of said bushing in a first direction is configured to be limited by said hooked head of said fastener.

4. The assembly system of claim 1, wherein said fastener further comprises a neck, configured to be at least partially received by said counterbore, and sized to define a space disposed between an outer neck surface and said inner uppermost surface.

5. The assembly system of claim 1, wherein at least a portion of said aperture includes an internally threaded portion.

6. The assembly system of claim 5, wherein said internally threaded portion is disposed between said inner uppermost surface and said opposing end surface.

7. In combination, an assembly system, comprising:
a taper seating connector including a fastener and a bushing, said fastener having a shaft and a head, said shaft having a threaded portion and a non-threaded portion, said threaded portion of said shaft adapted for threaded engagement to a first orthopedic component having one of a male tapered surface and a female tapered surface, said bushing having an external uppermost surface, an opposing end surface, and an aperture extending therethrough, said non-threaded portion of said shaft configured to be positioned at least partially within said aperture, said threaded portion of said shaft configured to be positioned entirely outside of said aperture adjacent to said end surface of said bushing, said head of said fastener configured to be positioned outside of said aperture adjacent to said external uppermost surface of said bushing and extending beyond a periphery of said bushing, whereby said head is configured to be available for securement, wherein said bushing is configured to be retained on and axially moveable along said non-threaded portion of said shaft of said fastener, said bushing configured to be moveable along said non-threaded portion of said shaft between a first position in which said head of said fastener contacts said external uppermost surface of said bushing and a second position in which a thread of said threaded portion of said shaft contacts said end surface of said bushing, said bushing configured to be positioned adjacent to a second orthopedic component when said fastener is connected to said first orthopedic component, said second orthopedic component having the other of said one of a male tapered surface and a female tapered surface; and a taper seating tool having a rod and a sleeve, said rod configured for selective attachment to said fastener of said taper seating connector, said sleeve configured to selectively abut said bushing of said taper seating connector when said rod is attached to said fastener, whereby movement of at least one of said rod and said sleeve relative to the other of said rod and said sleeve seats said male tapered surface and said female tapered surface.

8. The assembly system of claim 7, wherein said rod is fixed and said sleeve is configured to be moveable relative to the rod.

9. The assembly system of claim 7, wherein said head is a hooked head and said rod of said taper seating tool further comprises a transverse bar, said hooked head sized to receive said transverse bar.

10. The assembly system of claim 7, wherein said taper seating tool further comprises a fixed handle connected to said rod, a moveable handle connected to said sleeve, said moveable handle operable to actuate said sleeve relative to said rod, and a lock arm, said lock arm forming a connection between said fixed handle and said moveable handle, said lock arm capable of restricting the movement of said moveable handle in at least one direction.

11. A method of seating orthopedic components comprising the steps of:
securing a taper seating connector to a first orthopedic component, the taper seating connector comprising:
a fastener and a bushing, the fastener having a shaft and a head, the shaft having a threaded portion and a non-threaded portion, the bushing having an external uppermost surface, an opposing end surface, and an aperture extending therethrough, the non-threaded portion of the shaft of the fastener positioned at least partially within the aperture of the bushing, the threaded portion of the shaft positioned entirely outside of the aperture adjacent to the end surface of the bushing, the head of the fastener positioned outside of the aperture adjacent to the external uppermost surface of the bushing and extending beyond a periphery of said bushing, whereby said head is available for securement, wherein the bushing is retained on and axially moveable along the non-threaded portion of the shaft of the fastener, wherein the taper seating connector is secured to the first orthopedic component by threadingly engaging the threaded portion of the fastener with the first orthopedic component;
positioning the opposing end surface of the taper seating connector adjacent to a second orthopedic component;
providing a taper seating tool that is independent of the taper seating connector;
attaching the taper seating tool to the head of the fastener of the taper seating connector; and actuating the taper seating tool to advance the bushing of the taper seating connector along the non-threaded portion of the shaft of the fastener of the taper seating connector to force the second orthopedic component toward the first orthopedic component to seat the first and second orthopedic components.

12. The method of claim 11, wherein the first orthopedic component comprises a tibial keel and the second orthopedic component comprises a tibial plate.

13. The method of claim 11, further comprising the step of cementing the first orthopedic component to a bone.

* * * * *